US006605738B1

United States Patent
Ho et al.

(10) Patent No.: US 6,605,738 B1
(45) Date of Patent: Aug. 12, 2003

(54) PROCESSES FOR REFINING BUTYL ACRYLATE

(75) Inventors: Fungau Ho, Charleston, WV (US); Vivek Julka, Dunbar, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 687 days.

(21) Appl. No.: 08/859,143

(22) Filed: May 20, 1997

Related U.S. Application Data (60) Provisional application No. 60/018,538, filed on May 29, 1996.

(51) Int. Cl.⁷ .............................................. C07C 67/48
(52) U.S. Cl. ..................................... 560/218; 560/205
(58) Field of Search ................................ 560/218, 205

(56) References Cited

U.S. PATENT DOCUMENTS

| | | | |
|---|---|---|---|
| 3,700,726 A | 10/1972 | Johnson, Jr. et al. | 260/491 |
| 3,875,212 A | 4/1975 | Ohrui et al. | 260/486 |
| 3,882,167 A | 5/1975 | Lohmar et al. | 260/486 |
| 4,012,439 A | 3/1977 | Erpenbach et al. | 260/486 |
| 4,076,950 A | 2/1978 | Stewart et al. | 560/218 |
| 4,202,990 A | 5/1980 | Murakami et al. | 560/217 |
| 4,280,010 A | 7/1981 | Erpenbach et al. | 560/205 |
| 4,474,981 A | 10/1984 | Katoh et al. | 560/205 |
| 4,814,493 A | 3/1989 | Dougherty et al. | 560/205 |
| 4,833,267 A | 5/1989 | Nakashima et al. | 560/205 |
| 5,093,520 A | 3/1992 | Nestler et al. | 560/218 |
| 5,231,222 A | 7/1993 | Papa et al. | 560/265 |
| 5,302,747 A | 4/1994 | Nelson et al. | 560/265 |

FOREIGN PATENT DOCUMENTS

| | | |
|---|---|---|
| EP | 424861 | 10/1989 |
| JP | 2279655 | 11/1990 |

OTHER PUBLICATIONS

Kirk–Othmer, Encylcopedia of Chemical Technology, fourth edition, vol. 8, pp. 333, Nov. 1993.*
Aldrich Catalog, p. 225, 1992.*
Kirk Othmer, "Encyclopedia of Technology", Third Edition, vol. I, 1978, pp. 330–354.

* cited by examiner

*Primary Examiner*—Samuel Barts
*Assistant Examiner*—Elvis O. Price (57) ABSTRACT

Crude butyl acrylate streams, e.g., from the reaction of butanol and acrylic acid, are refined using a splitter distillation column to yield a butyl acrylate- and heavies-containing bottoms fraction and an overhead fraction containing dibutyl ether, butyl acetate, butanol and butyl acrylate. The bottoms fraction is then subjected to separation, e.g., by distillation, to separate heavies from the bottoms fractions and to recover butyl acrylate. A process for the production of butyl acrylate is also disclosed, which process comprises not only the above-mentioned refining steps but also includes the steps of withdrawing from the splitter distillation column the overhead fraction and distilling the overhead fraction to recover a bottoms stream containing butanol and butyl acrylate, at least a portion of which could be recycled for reaction with acrylic acid to make butyl acrylate, and recovering the separated heavies, at least a portion of which could be recycled to a reaction zone for the production of butyl acrylate. At least 10,000 lb(avoir) quantities of a butyl acrylate product comprising at least 99.8 wt % butyl acrylate and containing not more than about 200 ppm butyl ether and not more than about 200 ppm butyl acetate are producible.

17 Claims, 1 Drawing Sheet

THE FIGURE

PROCESSES FOR REFINING BUTYL ACRYLATE

This application claims the benefit of provisional U.S. patent application Ser. No. 60/018,538, filed May 29, 1996.

FIELD OF THE INVENTION

This invention pertains to processes for producing n-butyl acrylate by the esterification of acrylic acid with n-butanol and to processes for refining butyl acrylate. In accordance with this invention, a splitter distillation column is used to make a separation between (i) lights, which include dibutyl ether, butyl acetate, butanol and lower boiling components and (ii) acrylate and heavies.

BACKGROUND OF THE INVENTION

Butyl acrylate is prepared by the equilibrium-limited reaction of acrylic acid-and n-butanol. The reaction is conducted at elevated temperature in the presence of a catalyst. Typically, the coproduct, water, is removed during the course of the reaction to drive the reaction more toward the butyl acrylate product. In conducting this reaction, impurities in the raw materials and side reactions generate by-products that must be removed from the butyl acrylate.

Conventionally, the refining of the butyl acrylate-containing reaction product is conducted by distillation. The purification is generally done in several distillation column sections. U.S. Pat. No. 4,012,439 discloses a process for producing n-butyl acrylate free from dibutyl ether. In the disclosed process, the esterification reaction product is sent to a first distillation column. A ternary mixture containing butyl acrylate, butanol and water is the distillate. This distillate is condensed and subjected to phase separation, and the organic phase is delivered to a second distillation column from which a ternary distillate of butyl acrylate, butanol and water is obtained. The base product from this second distillation column contains butanol and butyl acrylate and is passed to a third distillation column for the separation of butanol from butyl acrylate.

U.S. Pat. No. 4,280,010 discloses a process for making butyl acrylate in which the reaction overhead is passed to a reactor column with the distillate being a butyl acrylate, butanol and water azeotrope. A reflux is used in the reactor column. The remainder of the distillate is sent to a dehydration column and the organic product is further distilled to provide a butanol—butyl acrylate azeotrope being recycled to the reactor and butyl acrylate stream being obtained at the base of the column.

U.S. Pat. No. 4,814,493 discloses another technique for making butyl acrylate. The reaction overhead is passed to a finishing distillation column. The finishing distillation column provides a side stream of butyl acrylate product, a bottoms stream that is recycled to the reactor and an overhead stream that is passed to a butanol recovery distillation column. The distillate from the butanol recovery column is recycled to the reactor. This patent also describes the use of a heat treater which receives a portion of the liquid from the reactor. The heat treater apparently cracks components which can then be separated from heavies via distillation column and returned to the reactor.

Butyl acrylate having high purity is sought. The process for making butyl acrylate, and the sources of raw materials for those processes, result in troublesome separations. One impurity is dibutyl ether which has a normal boiling point within 5° to 7° C. of that of butyl acrylate. This impurity can impart odor to the butyl acrylate. Another impurity is butyl acetate which is the esterification product of acetic acid, an impurity in acrylic acid, and butyl acetate can also impart odor to butyl acrylate.

Processes for manufacturing and refining butyl acrylate are sought which are economical, energy efficient and capable of providing butyl acrylate of enhanced purity. Moreover, processes are sought that enable the use of acrylic acid containing acetic acid and reaction conditions which enable dibutyl ether to be formed, yet provide a butyl acrylate product to be obtained of unexpectedly high purity.

SUMMARY OF THE INVENTION

In accordance with the processes of this invention, a fluid stream containing butyl acrylate, dibutyl ether, butyl acetate, and n-butanol is separated in a splitter distillation column to provide an overhead fraction containing dibutyl ether, butyl acetate and butanol and a bottoms fraction containing butyl acrylate and heavies. The overhead fraction typically contains butyl acrylate in addition to dibutyl ether, butyl acetate and butanol. The bottoms fraction preferably contains less than about 0.2 weight percent of total dibutyl ether and butyl acetate and less than about 10 percent of the total dibutyl ether and butyl acetate in the fluid stream. The overhead fraction from the splitter column is subjected to further distillation in the presence of water in a butanol recovery column to separate butanol and butyl acrylate from lights containing dibutyl ether and butyl acetate. The bottoms fraction from the splitter distillation column, comprising heavies and butyl acrylate, can advantageously be rectified in a butyl acrylate distillation column to separate heavies from the butyl acrylate.

In the aspect of the invention relating to esterification processes, n-butanol and acrylic acid are subjected, in at least one reaction zone, to esterification reaction conditions including the presence of an esterification catalyst, to produce butyl acrylate and water as well as side products including butyl acetate, heavies and dibutyl ether. A gaseous stream containing water, butanol, acrylic acid, butyl acrylate, butyl acetate, dibutyl ether and heavies is withdrawn from the reaction zone and passed to a reactor distillation column. The overhead from the reactor distillation column contains water, butanol, butyl acrylate, butyl acetate, dibutyl ether and heavies, and this overhead is condensed and subjected to liquid phase separation to remove most of the water, and the resulting organic phase is the liquid feed stream to the splitter distillation column as described above. The bottoms fraction from the reaction distillation column is rich in acrylic acid, at least a portion of which is recycled to at least one reaction zone.

The bottoms fraction from the splitter distillation column is advantageously rectified in a distillation column to separate heavies from the butyl acrylate. Recovered butyl acrylate has a purity of at least about 99.0 weight percent butyl acrylate, less than about 1000, more preferably less than about 200, and most preferably less than about 60, parts per million by weight (ppmw) dibutyl ether and preferably less than about 500, more preferably less than about 50, ppmw butyl acetate, with the sum of dibutyl ether, and butyl acetate preferably being less than about 1500 ppm. More preferably, the recovered butyl acrylate has a purity of at least about 99.5, more preferably at least about 99.8, and most preferably 99.9, weight percent butyl acrylate and less than about 400, and most preferably less than about 300, ppmw of total dibutyl ether and butyl acetate. At least a portion of the recovered heavies can be recycled to at least one esterification reaction zone or supplied to another reaction zone to crack the heavies and regenerate butanol and acrylic acid.

DETAILED DESCRIPTION OF THE INVENTION

Butyl acrylate is manufactured by the equilibrium-limited liquid phase reaction of n-butanol and acrylic acid. The reaction may be conducted as a batch process, but is preferably conducted as a continuous process in which the reactants and any adjuvants such as catalysts, inhibitors and solvents, are added periodically or uninterruptedly to, and products are removed periodically or uninterruptedly from, one or more reaction zones.

The reaction is typically conducted at temperatures within the range of about 70° to 170° C., more typically in the range of about 80° to 150° C. and most preferably in the range of about 90° to 140° C., but below a temperature that causes undue degradation of the reactants or butyl acrylate and a temperature that causes the formation of polymer by reaction of the unsaturated moiety in acrylic acid.

The pressure at which the reaction is carried out also varies widely. Typically, reaction zone pressures range from subatmospheric to superatmospheric, e.g., from about 0.01 to 5 bar, more often from 0.1 to 2 bar, and most often from about 0.1 to 1.5 bar, absolute.

Catalysts appropriate for the reaction can be used and can be heterogeneous or homogeneous. Catalysts include acids such as sulfuric acid, sulfonic acids, and ion exchange resins having acidic functionality. The amount of catalyst can vary widely and often is in the range of about 0.001 to 20 weight percent of the liquid menstruum.

The reaction may be conducted in the presence of a solvent or, one or more of the reactants, products, coproducts and side reaction products may comprise the liquid media for the reaction. Where a solvent is used, it is preferably substantially inert and is substantially non-volatile under reaction conditions. Other adjuvants may be contained in the liquid reaction media, such as antioxidants, stabilizers, buffers, and the like.

The relative amounts of the reactants fed to the reaction zone may also vary widely and will often be selected based upon economic factors. Typically, reactants are supplied as fresh feed and recycle feed. Generally, the fresh feed butanol and acrylic acid is supplied in an approximately stoichiometric ratio for producing the desired product, plus any additional amounts required to make up for losses due to side reactions. Often, the mole ratio of the butanol to acrylic acid is between about 0.8:1 to about 1.2:1. Most preferably, as much as 90% of the fresh feed is consumed in the reaction zone. It should be understood that the amount of the reactants, and their relative concentrations, in the reaction zone may be different than that of the fresh feed due to recycling of unreacted reactants, with the mole ratio of butanol to acrylic acid ranging from about 0.5:1 to about 5:1 and most preferably ranging from about 0.9:1 to about 1.5:1.

The esterification process of this invention is conducted in at least one liquid phase reaction zone. More than one reaction zone, or reaction stage, can be used. When more than one reaction zone is used, the reaction menstruum may be the same or different in each reaction zone.

In one embodiment of the invention, the conversion of the butanol and acrylic acid to butyl acrylate occurs in a single reactor. The butyl acrylate produced in the reactor may be withdrawn as a liquid product stream from the reaction menstruum or removed as a gaseous product. If the product stream is withdrawn from the reaction menstruum as liquid, the conditions of the reaction zone should be such that the theoretical vapor-liquid equilibrium provides for at least about 50, preferably at least about 70 and more preferably at least about 80, percent of the butyl acrylate contained in the reaction vessel to be in the liquid phase. The temperature and pressure should also be sufficient to drive the water to the gas phase so that gases removed from the reaction zone will be an azeotropic mixture. Often, under the conditions of the reaction zone including those promoting azeotrope formation, the vapor-liquid equilibrium for the reactants is such that at least about 50, preferably at least about 70, percent of each reactant contained in the reaction vessel is in the liquid phase. If it is elected to take the product stream as a gaseous effluent from the reaction zone, the conditions of the reaction zone should also be such that the theoretical vapor-liquid equilibrium provides for at least about 40, preferably at least about 50, and more preferably at least about 60 percent of the butyl acrylate contained in the vessel to be in the vapor phase.

Regardless of how the product stream is taken from the reaction zone, it will contain butanol, acrylic acid, butyl acrylate and water and impurities such as heavies, dibutyl ether, and butyl acetate.

In a single reactor process, azeotropic mixture produced in a liquid phase product production and removal regimen is removed from the reactor and typically subjected to liquid phase separation to remove the water, with at least a portion of the organic liquid comprising unreacted reactants being recycled to the reactor. Under gas phase product removal reaction conditions, the gaseous product stream removed from the reactor is subjected to distillation to return reactants to the reaction zone. The overhead from the distillation column is subjected to condensation and liquid phase separation to remove water, and a portion of the liquid is returned to the distillation column as reflux and the remaining organic phase is refined.

In another embodiment of the process, sequential reaction zones are employed. In this embodiment, liquid is withdrawn from a first reaction zone, which liquid contains product, co-product and unreacted reactants. While, in many instances, essentially all of the liquid withdrawn from the first reaction zone is passed to a second reaction zone, the broad concept contemplates using a portion of the liquid stream for other processing. In either case, additional reactant can be provided to the secondary reaction zone as a fresh feed or via a recycle stream. Also, an intervening separation step may be used to separate product and/or coproduct from the liquid. The separation may simply be a liquid phase separation to remove, e.g., water via a flashing or distillation unit operation, or coproduct or product separation via a membrane separation or a sorption process.

Sequential reactor zones provide process flexibility. For instance, no overhead stream need be removed from the first reaction zone. Thus, a plug flow reactor could be used if desired. Generally, the residence time of the liquid menstruum in the primary reaction zone is sufficient to produce butyl acrylate at a concentration to within 50, typically, within about 70, and sometimes at least about 90 or 95, percent of the theoretical equilibrium concentration of butyl acrylate in the reaction menstruum under the conditions of the reaction (for given reactant concentrations). Because no overhead stream need be taken, savings in equipment and energy can be achieved. The reaction can proceed further in the second reaction zone to achieve the desired amount of conversion. Advantageously, at least about 50, preferably at least about 70, and most preferably between about 75 and 90, percent of the total amount of butyl acrylate produced in the process is produced in the first reaction zone. Often, the first reaction zone is operated such that an amount equivalent to at least about 50, preferably at least about 70, and most preferably between about 75 and 90, percent of the fresh feed of at least one, most preferably both, of the reactants is consumed in the primary reaction zone.

The conditions of the second reaction zone are maintained such that the butyl acrylate product is vaporized. The conditions may include a temperature and pressure such that the product flashes into the gaseous phase. Preferably, under the conditions of the second reaction zone including azeotrope formation, the vapor-liquid equilibrium for butyl acrylate is such that less than about 50, preferably less than about 30, percent of butyl acrylate contained in the reaction vessel is in the liquid phase. Also, under the conditions of the second reaction zone including azeotrope formation, the vapor-liquid equilibrium for butanol and acrylic acid preferably is such that less than about 50, and in some instances less than about 30, percent of at least one of the reactants contained in the reaction vessel is in the liquid phase.

Often the second reaction zone is at temperatures within the range of about 80° to 170° C., more typically within the range of about 90° to 150° C., but below a temperature that causes undue degradation of the reactants or butyl acrylate. Preferably, the temperature of the liquid menstruum in the second reaction zone is equal to or greater, e.g., 0° to about 15° C. greater, than the temperature of the menstruum in the first reaction zone. The pressure in the second reaction zone can also vary widely. Typically, pressures range from subatmospheric to superatmospheric, e.g., from about 0.01 to 5 bar, most often from about 0.1 to 1.5 bar, absolute. Often, the pressure in the second reaction zone is equal to or below the pressure in the first reaction zone, e.g., about 0 to 0.9 bar below the pressure in the first reaction zone.

The reaction in the second reaction zone is conducted in the presence of liquid comprising at least one of butanol, acrylic acid, heavies, and one other liquid component, e.g., a solvent. The reaction menstruum may be the same or different in the first reaction zone and in the second reaction zone. Where a solvent is used, it is preferably substantially inert and is substantially non-volatile under reaction conditions. Even though butanol and acrylic acid will be vaporized, the reactants are maintained in the liquid of the second reaction zone for a time sufficient to produce butyl acrylate. A gas is withdrawn from the second reactor and comprises butanol, acrylic acid, butyl acrylate, water and impurities such as heavies, dibutyl ether and butyl acetate.

Catalysts appropriate for the equilibrium reaction can be used in the second reaction zone and may be the same or different catalyst used in the first reaction zone. Advantageously, if the catalyst in the first reaction zone is a homogeneous catalyst or a slurried heterogeneous catalyst, it can be passed with the liquid to the second reaction zone. Alternatively, the use of a heterogeneous, stationary catalyst in the first reaction zone, enables a different catalyst to be used in the second reaction zone.

Heavies are formed by a Michael reaction and as depicted by the following equation:

Acrylic Acid+Butanol+Butyl Acrylate⊖→Heavies

The heavies product (including dimer) is typically an equilibrium product. The heavies may comprise a substantial portion of the liquid menstruum; for instance, at least about 10, more typically, about 20 to 90 or more, weight percent of the menstruum. In such an embodiment, acrylic acid and butanol can be recovered as a bottoms fraction, and at least a portion of the bottoms fraction can be recycled to at least one of the first or second reaction zones. Advantageously, the second reaction zone can be operated under conditions favorable to cracking the heavies.

In accordance with this invention, the crude butyl acrylate stream withdrawn from the reaction zone and typically containing dibutyl ether, butyl acetate, butanol, water and heavies is refined by distillation in a splitter distillation column which produces an overhead fraction containing dibutyl ether, butyl acetate and butanol and a bottoms fraction containing butyl acrylate heavies and preferably less than about 1000 ppmw of total butyl acetate and dibutyl ether.

The actual compositional make-up of the reaction zone product stream depends on a number of factors. For example, the composition of the crude butyl acrylate stream depends, in part, upon the composition of the reactants. Impurities in the feeds will also influence the composition; for instance, acetic acid is often an impurity in acrylic acid and butyl acetate will be generated in the reaction zone. Advantageously, if desired, the processes of this invention enable a mixed acetic acid and acrylic acid feed to be used to co-generate butyl acetate and butyl acrylate, both valuable products. Further, whether the crude stream is recovered as a gaseous effluent affects composition. Moreover, catalysts and other adjuvants used also affect the composition. In general, the crude stream will often be comprised of the components listed in Table 1, below:

TABLE 1

| Component | Typical Ranges, weight percent | Preferred, weight percent |
| --- | --- | --- |
| Butyl Acrylate | 40 to 98 | 75 to 95 |
| Butyl Acetate | 0.01 to 50 | 0.05 to 0.2 |
| Butanol | 1 to 50 | 3 to 20 |
| Acrylic Acid | 0 to 5 | 0 to 0.002 |
| Dibutyl Ether | 0.001 to 25 | 0.05 to 0.15 |
| Heavies | 0 to 25 | 0.05 to 5 |
| Water | 0 to 50 | 0.5 to 3 |

The crude stream will generally contain a total of at least about 0.05 weight percent of total butyl acetate and dibutyl ether, and often will contain at least about 0.1, and up to about 55, weight percent of total butyl acetate and dibutyl ether.

If water is present to form azeotropes, as is usually and preferably the case, the crude stream will actually be comprised of a wide variety of constituents including several azeotropes containing one or more of the above-mentioned components. Table 2, below, summarizes the principal components including azeotropes that may be present in the crude stream supplied to the splitter distillation column.

TABLE 2

| Component or Azeotrope | Composition (wt. %) | Normal Boiling Point (° C.) |
| --- | --- | --- |
| Water/BuOH/BuAc/BE | 30/13/51/6 | 90.6 |
| Water/BuOH/BE | 29.9/34.6/35.5 | 90.6 |
| Water/BuOH/BuAc | 29/8/63 | 90.7 |
| Water/BuAc | 27.1/72.9 | 90.7 |
| Water/BuOH/BA | 50/37.6/12.4 | 92.0 |
| Water/BuOH | 44.5/55.5 | 93.0 |
| Water/BE | 33.4/66.6 | 94.1 |

TABLE 2-continued

| Component or Azeotrope | Composition (wt. %) | Normal Boiling Point (° C.) |
|---|---|---|
| Water/BA | 38/62 | 94.3 |
| Water | | 100.0 |
| BuOH/BuAc | 67.2/32.8 | 117.6 |
| BuOH/BE | 82.5/17.5 | 117.6 |
| BuOH | | 117.7 |
| BuAc | | 126 |
| BE | | 142.5 |
| BA | | 148.8 |

BuOH = Butanol
BuAc = Butyl Acetate
BE = Dibutyl Ether
BA = Butyl Acrylate

The number of theoretical plates in the splitter distillation column will vary depending upon the composition of the crude stream and the desired concentration of the butyl acrylate in the bottoms stream. For example, the separation of butyl acrylate from formed azeotropes of butyl acetate and dibutyl ether requires less theoretical plates than that required for the separation of butyl acrylate from butyl acetate and dibutyl ether. Generally, the splitter column will have at least about 10 or 12 theoretical plates, more typically, between about 15 and 30 theoretical plates. The number of theoretical plates is preferably sufficient to provide a bottoms fraction containing less than 1500, preferably less than about 500, ppmw of total butyl acetate and dibutyl ether. The point of feed to the splitter column will also depend upon the crude stream composition. For streams supplied directly from the esterification reaction zone, the feed to the splitter column is frequently at a point that permits at least about 5 theoretical plates to exist below the point of feed. The splitter column may be of any suitable design, including trays, packing or a combination of trays and packing. The splitter column is generally operated with a reflux ratio of between about 1 and 50. The reflux ratio is generally selected based upon the composition of the crude stream and the desired separation.

The temperature and pressure of the splitter distillation column will also depend upon the sought separation. Often, the splitter column is operated at subatmospheric pressure in order that the separation can be effected at temperatures below those that can result in degradation or side reactions of any of the components in the feed stream. The pressure at the base of the splitter column typically ranges from about 0.01 to 1.1, preferably from about 0.1 to 0.8, bar absolute. The temperature at the base of the splitter column is generally within the range of about 80° to 150° C., preferably 90° to 130° C. The pressure at the top of the splitter column typically is between 0.01 and 0.8, typically, 0.05 to 0.6, bar below the pressure at the base of the splitter column. The temperature at the top of the splitter column is generally about 40° to 110° C., preferably 50° to 100° C.

In preferred embodiments of this invention, water is present in the column. Generally, sufficient water is present to form azeotropes with at least 70, preferably essentially 100, percent of the total butyl acetate and dibutyl ether in the crude stream. Often the water is at approximately the saturation concentration in the crude stream. Water can be added to the column to enhance the formation of any desired azeotropes to effect the distillative separation. Where water is present, the use of a decanter to treat the overhead may be desired. The organic phase can be used to provide reflux and the aqueous fraction discarded, Alternatively, at least a portion of the aqueous phase may be used in the splitter column or the butanol recovery column to promote the desired azeotrope formation.

The composition of the bottoms fraction from the splitter distillation column is often as set forth in Table 3, below:

TABLE 3

| Component | Typical Ranges (wt. %) | Preferred (wt. %) |
|---|---|---|
| Butyl Acrylate | 75 to 100 | 95 to 99.999 |
| Butyl Acetate | 0.000 to 0.1 | 0.000 to 0.05 |
| Butanol | 0.000 to 5 | 0.000 to 0.1 |
| Acrylic Acid | 0.000 to 5 | 0.000 to 0.1 |
| Dibutyl Ether | 0.000 to 0.1 | 0.000 to 0.02 |
| Heavies | 0.000 to 25 | 0.5 to 5 |
| Water | 0.000 to 10 | 0.000 to 0.1 |

The composition of the overhead fraction from the splitter distillation column is typically made up of the components recited in Table 4, below:

TABLE 4

| Component | Typical Ranges (wt. %) | Preferred (wt. %) |
|---|---|---|
| Butyl Acrylate | 10 to 50 | 20 to 30 |
| Butyl Acetate | 0.000 to 30 | 0.3 to 4 |
| Butanol | 20 to 80 | 50 to 70 |
| Acrylic Acid | 0.000 to 5 | 0.000 to 0.002 |
| Dibutyl Ether | 0.000 to 20 | 0.3 to 4 |
| Heavies | 0.000 to 0.1 | 0.000 to 0.001 |
| Water | 0.000 to 50 | 4 to 10 |

The total dibutyl ether and butyl acetate in the overhead fraction is generally at least about 100 ppmw, and often is in the range of about 0.1 to 10, preferably about 0.5 to 8, weight percent of the overhead fraction.

The overhead fraction is subjected to a further distillation in a butanol recovery column. Advantageously, the recovered butanol is sufficiently free from dibutyl ether and butyl acetate that it is desirably recycled to an esterification reaction zone. The butanol recovery column is operated in the presence of water to form azeotropes such that butanol is recovered as a bottoms stream. The amount of water present should be sufficient such that at least about 70, most preferably essentially 100, percent of the total butyl acetate and dibutyl ether forms an azeotrope. The number of theoretical plates in the butanol recovery column will vary depending upon the composition of the portion of the overhead stream from the splitter column that is passed to the butanol recovery column and the desired purity of the butanol. Generally, the butanol recovery column will have at least about 5 theoretical plates, preferably, between about 7 and 20 theoretical plates. The number of theoretical plates is preferably sufficient to provide a bottoms fraction containing less than about 5000, more preferably less than about 3000, ppmw of total dibutyl ether and butyl acetate. Frequently, from 2 to about 16 theoretical plates are provided below the point of the feed to the butanol recovery column. The butanol recovery column may be of any suitable design, including trays, packing or a combination of trays and packing. The butanol recovery column is generally operated with a reflux ratio of between about 1 and 60. The temperature and pressure of the column will depend upon the sought separation.

Often, the column is operated at subatmospheric pressure in order that the separation can be effected at temperatures below those that can result in degradation or side reactions of any of the components in the feed stream. The pressure at the base of the column typically ranges from about 0.01 to 1.1, preferably from about 0.1 to 0.8, bar absolute. The temperature at the base of the butanol recovery column is generally within the range of about 50° to 120° C., preferably 60° to 100° C.

The composition of the bottoms fraction from the butanol recovery column is often as set forth in Table 5, below:

TABLE 5

| Component | Typical Ranges (wt. %) | Preferred (wt. %) |
| --- | --- | --- |
| Butyl Acrylate | 5 to 50 | 18 to 30 |
| Butyl Acetate | 0.000 to 10 | 0.000 to 0.4 |
| Butanol | 20 to 80 | 65 to 75 |
| Acrylic Acid | 0.000 to 5 | 0.000 to 0.01 |
| Dibutyl Ether | 0.000 to 5 | 0.000 to 0.1 |
| Heavies | 0.000 to 1 | 0.000 to 0.3 |
| Water | 0.1 to 50 | 2 to 8 |

The composition of the overhead fraction from the butanol recovery column is typically made up of the components recited in Table 6, below:

TABLE 6

| Component | Typical Ranges (wt %) | Preferred (wt. %) |
| --- | --- | --- |
| Butyl Acrylate | 1 to 50 | 3 to 30 |
| Butyl Acetate | 0.000 to 80 | 10 to 60 |
| Butanol | 10 to 70 | 25 to 40 |
| Acrylic Acid | 0.000 to 2 | 0.000 to 0.005 |
| Dibutyl Ether | 0.000 to 40 | 5 to 30 |
| Heavies | 0.000 to 0.1 | 0.000 to 0.005 |
| Water | 1 to 50 | 2 to 8 |

The total butyl acetate and dibutyl ether in the overhead fraction from the butanol recovery column is often at least about 5 and can comprise up to about 80, weight percent of the overhead fraction. Since water is used in the distillation process, the overhead from the butanol recovery column is often subjected to phase separation. The organic phase can be used to provide reflux and the aqueous fraction discarded. Alternatively, at least a portion of the aqueous fraction may be recycled to the butanol recovery column to promote the desired azeotrope formation.

The bottoms fraction from the splitter distillation column contains butyl acrylate and heavies. This bottom fraction may be acceptable as is or may be further processed in a butyl acrylate separation column to remove the heavies. The separation may be a flash separation in which a butyl acrylate stream is taken overhead, or may be a distillation. Generally, the butyl acrylate separation column will have at least 2 theoretical plates, typically 3 to about 10 theoretical plates. The butyl acrylate separation column may be of any suitable design, including trays, packing or a combination of trays and packing. The butyl acrylate separation column is generally operated with a reflux ratio of between about 0.05 and 10. The temperature and pressure of the column will depend upon the sought separation. Often, the separation column is operated at subatmospheric pressure in order that the separation can be effected at temperatures below those that can result in degradation or side reactions of any of the components in the feed stream. The pressure at the base of the separation column typically ranges from about 0.01 to 1.1, preferably from about 0.02 to 0.8, bar absolute. The temperature at the base of the butyl acrylate column is generally within the range of about 60° to 170° C., preferably 70° to 150° C.

The composition of the bottoms fraction from the butyl acrylate separation column is often as set forth in Table 7, below:

TABLE 7

| Component | Typical Ranges (wt. %) | Preferred (wt. %) |
| --- | --- | --- |
| Butyl Acrylate | 5 to 99 | 10 to 98 |
| Butyl Acetate | 0.000 to 0.1 | 0.000 to 0.05 |
| Butanol | 0.000 to 0.1 | 0.000 to 0.001 |
| Acrylic Acid | 0.000 to 0.05 | 0.000 to 0.01 |
| Dibutyl Ether | 0.000 to 0.1 | 0.000 to 0.05 |
| Heavies | 5 to 95 | 10 to 90 |
| Water | 0.000 to 1 | 0.000 to 0.02 |

The composition of the overhead fraction from the butyl acrylate separation column is typically as recited in Table 8, below:

TABLE 8

| Component | Typical Ranges (wt. %) | Preferred (wt. %) |
| --- | --- | --- |
| Butyl Acrylate | 95.0 to 100 | 99.5 to 100 |
| Butyl Acetate | 0.000 to 0.05 | 0.000 to 0.01 |
| Butanol | 0.000 to 0.01 | 0.000 to 0.01 |
| Acrylic Acid | 0.000 to 5 | 0.000 to 0.01 |
| Dibutyl Ether | 0.000 to 0.1 | 0.000 to 0.02 |
| Heavies | 0.000 to 2 | 0.000 to 0.5 |
| Water | 0.000 to 0.5 | 0.000 to 0.05 |

In an advantageous aspect of the invention, at least a portion of the bottoms fraction from the butyl acrylate separation column is passed to a reactor operating under cracking conditions to recover acrylic acid and butanol. As previously disclosed, the processes that use sequential reactors can be operated such that the second reaction zone is at a temperature and contains heavies in sufficient concentration such that cracking of the heavies is facilitated.

Although the foregoing discussion has referenced a splitter distillation column in combination with a butanol recovery column and a butyl acrylate separations column, this invention contemplates the use of a single splitter distillation column with a plurality of reflux and off take locations to accomplish the separations effected by the recovery and separation columns.

Figure 1:
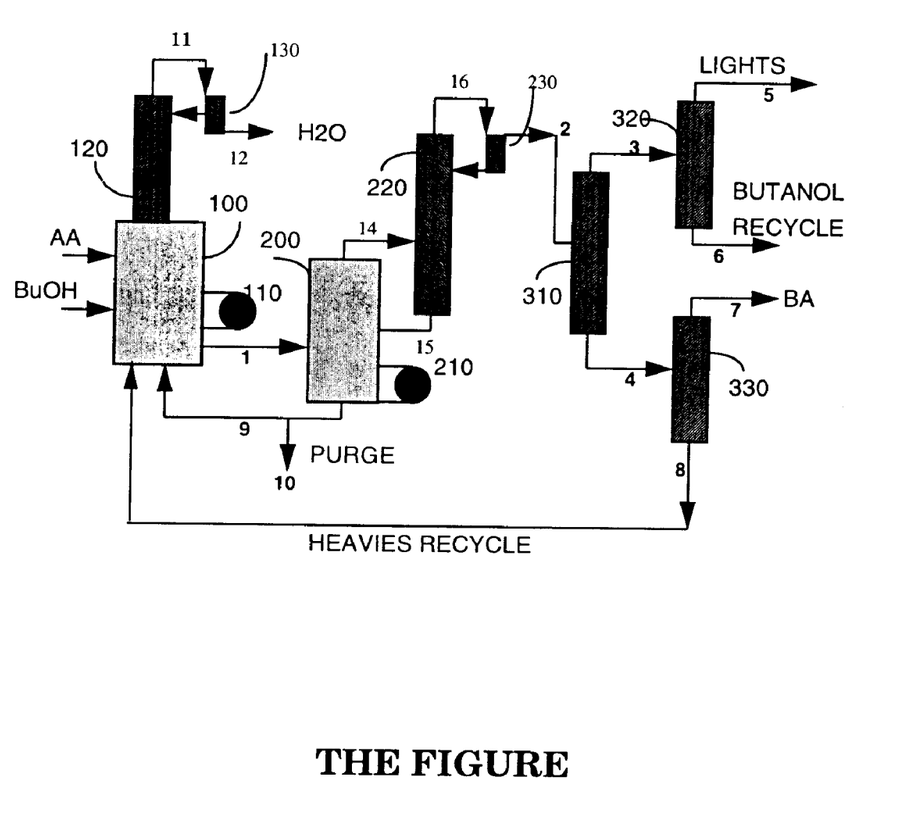
FIG. 1 is a schematic depiction of a process for making butyl acrylate from acrylic acid and butanol in accordance with this invention.

A preferred embodiment of the processes of this invention will be further described with reference to FIG. 1. In this embodiment, the esterification of acrylic acid with n-butanol, in the presence of an homogeneous acidic catalyst, to produce butyl acrylate is effected in sequential reaction zones.

Fresh acrylic acid and butanol are fed to a first reactor 100 in approximately equimolar amounts. The acrylic acid and butanol supplied to the reactor 100 are typically of standard purities. However, as a result of the processes of the present invention, higher concentrations of typical impurities in the acrylic acid stream are better tolerated. For example, the acrylic acid feed to reactor 100 may contain up to 0.2 or more weight percent acetic acid because the acetic acid can react with butanol to form butyl acetate, a light component that can be readily removed by employing the present invention. Other impurities, such as acrylic acid dimer, commonly present in the acrylic acid feed, are also tolerated: dimer, for example, is readily cracked by the high temperature operation of the second reactor 200, as discussed below. Similarly, as a result of the unique refining scheme, it is possible to easily remove dibutyl ether, the main impurity in butanol, which allows the use of a lower grade butanol feed. The ability to use a wide range of acid and alcohol leads to significant economic savings.

The butanol: acrylic acid molar ratio of the fresh feed to reactor 100 is approximately equimolar (1:1).

The reaction is carried out in the presence of an acidic catalyst. Examples include sulfuric acid, phosphoric acid, and resins that contain acid functional groups. Preferably, the catalyst is a long chain alkyl benzene sulfonic acid such as dodecylbenzene sulfonic acid (DBSA). DBSA catalyst and variations of it are described in U.S. Pat. No. 5,231,222. Relative to other catalysts, DBSA generates significantly less dibutyl ether and heavies during the esterification of acrylic acid with butanol; hence, higher efficiencies are achieved with DBSA as a result of low dibutyl ether and heavies formation. However, DBSA is a homogeneous catalyst; thus, it is subject to entrainment. Nonetheless, the reaction is carried out using DBSA because, unlike conventional processes employing DBSA, which would require catalyst reclamation steps, in the present processes DBSA is simply cycled via lines 1 and 9 between reactors 100 and 200. The reactors 100 and 200 and supply lines 1 and 9 are constructed of materials resistant to corrosion by the acid catalyst.

The catalyst concentration can vary over a wide range. In reactor 100 the DBSA can vary from about 0.1 to 10, preferably about 0.5 to 2, weight percent of the liquid menstruum. Because DBSA is viscous, catalyst make-up to reactor 100 or 200 is provided a solution of the catalyst with acrylic acid, butanol, recycle liquid, or any other reactor feed stream.

Inhibitors are provided to reactor 100. The inhibitors include phenothiazine (PZ), hydroquinone (HQ), and monomethyl ether of hydroquinone (MEHQ). It is generally accepted that polymer formation occurs in areas where the temperature is high, such as the reactor and distillation columns, or in those areas where vapor condenses on cold surfaces. PZ is utilized in organic streams and HQ and/or MEHQ in water streams. The amount of inhibitors used depends on the process. The chemical inhibitors in reactor 100 will be about 50 to 10,000, e.g., about 500, ppmw by weight based upon the weight of the liquid menstruum.

Besides the chemical inhibitors, oxygen is added to reactor 100 to enhance the inhibition of polymer formation. Use of oxygen is well known in the art. The oxygen can be added as pure oxygen, as a mixture with an inert gas, or preferably as air. The oxygen is supplied by an air sparger provided at the bottom of the reactor (not shown).

Reactor 100 is a tank type reactor for the reaction of acrylic acid with butanol and removal water in order to force the equilibrium to acrylate. A conversion of about 80 to 85 percent is desired. A portion of the liquid reactor 100 is taken to calandria 110 for increasing the temperature of the liquid. calandria 110 is a conventional tube in shell vessel. The turnover rate must assure that the contents of the reactor are well agitated and more uniformly heated. Alternatively, a jacketed reactor designed to generate the requisite heat and provided with mechanical stirrers could be used in place of the tank reactor and calandria The temperature in reactor 100 can range from 80 to 170° C. but it is most preferred to maintain the temperature within the range of 120–130° C. The return stream from calandria 110 is therefore at a temperature about 5 to 10° C. higher. The average residence time in reactor 100 is about 2 to 3 hours. The pressure in reactor 100 is maintained at about atmospheric pressure.

The esterification reaction generates water which is removed overhead and supplied to the bottom of a distillation column 120. As stated before, removing water drives the reaction toward butyl acrylate. The distillation column 120 may be attached to the top of the reactor. Column 120 is of standard engineering design and can use trays or packing. To accommodate any entrainment of the DBSA catalyst, the bottom trays may need to be constructed of a metal which can handle highly corrosive liquid. To prevent polymerization and other fouling reactions in the distillation column 120, conventional inhibitors such as hydroquinone and phenothiazine are introduced throughout the column 120, diluted by butanol or some other process liquid.

The overhead from the distillation column 120 is removed via line 11 and supplied to a condenser/separator 130. In condenser/separator 130, the vapor is condensed and the liquid is phase separated, with the organic phase being returned to the distillation column 120 and the aqueous phase being sent via line 12 to disposal or to another column (not shown) to remove residual organics from the aqueous phase.

The liquid reaction menstruum from the reactor 100 is supplied via line 1 to reactor 200. Reactor 200 is a standard tank reactor equipped with an air sparger (not shown). A portion of the liquid in reactor 200 is taken to calandria 210 to increase the temperature of the liquid. The calandria 210 is a conventional tube in shell vessel. Thes turnover rate must assure that the contents of the reactor are well agitated and maintained at the desired temperature.

The operating temperature in reactor 200 is higher than reactor 100 and the preferred range is 130° to 140 ° C. The return stream from calandria 210 is about 5° to 15° C. higher than the preferred reactor temperature. The higher temperature not only facilitates the conversion of the remaining butanol and acrylic acid to product, but very importantly, under these conditions, enable the heavies to be cracked back to butyl acrylate, acrylic acid and butanol.

The operating pressure in reactor 200 is lower than the pressure in reactor 100, and the preferred range is about 200 to 600 mmHg absolute (about 0.3 to 0.8 bar absolute). The residence time in reactor 200 is approximately 2 to 3 hours. Water is fed to reactor 200 in order to maintain a concentration of about 1 weight percent of the liquid menstruum for effective catalyst operation. The concentration of catalyst in the second reactor is about 1 to 20, preferably about 5 to 15. , e.g., 10, weight percent based upon the weight of the liquid menstruum. As with reactor 100, inhibitor is added throughout reactor 200 to reduce polymerization.

The liquid bottom stream from reactor 200, which contains heavies and catalyst, is recycled via line 9 to reactor 100. The bottom stream from reactor 200 is richer in catalyst and heavies than reactor 100. It should also be noted that the inhibitor concentration is also greater than in the first reactor, due to the cycle of the heavies between reactors 100 and 200. A purge from this recycle stream can be taken via line 10. The unique reaction system of our process allows for the recycle of heavies, catalyst and inhibitors. In conventional processes the entire heavies stream containing the inhibitors is typically discarded. Thus the processes of this invention enable lower catalyst and inhibitor usage and reduced inhibitor and catalyst cost.

Butyl acrylate, water and lights are removed as a vapor from reactor 200 and supplied via line 14 to an intermediate point of a distillation column 220. The primary purpose of distillation column 220 is to recover butyl acrylate, essentially free of acrylic acid, from the vapor stream of reactor 200. A secondary purpose is to recover water which is flashed in the reactor 200 due to the heat load in the reactor 200 and the calandria 210. The overhead from distillation column 220 is supplied via line 16 to a condenser/separator 230, and the water phase and a portion of the organic phase are returned to the top of the distillation column 220. The remaining portion of the organic phase is sent via line 2 to splitter distillation column 310.

The base of column 220 is heated. The top of column 220 may be at a pressure of 300 mmHg absolute (about 0.4 bar absolute). The liquid at the bottom of column 220 contains about 60 weight percent water and 40 weight percent organics (mostly acrylic acid). This bottoms fraction is returned via line 15 to reactor 200. This recycle step assists in maintaining a water concentration of about 1 weight percent in reactor 200

The feed for splitter distillation column 310 is the organic stream from distillation column 220, which consists mainly of butyl acrylate along with some butanol, lights, and heavies. The purpose of splitter distillation column 310 is, as described earlier, to separate the stream into a tails fraction containing butyl acrylate and heavies, and an overhead stream of butanol, butyl acrylate, and lights such as dibutyl ether and butyl acetate. The tails fraction is essentially free of all light components. The column design is consistent with conventional engineering practice and can use packing or trays. In this embodiment, the base temperature of the splitter distillation column 310 is about 120° C. with a pressure of about 400 mmHg (0.6 bar absolute).

The overhead stream from splitter distillation column 310 is supplied via line 3 to distillation column 320. Distillation column 320 separates the overhead stream into a tails stream consisting essentially of butanol and butyl acrylate and an overhead stream consisting essentially of lights, mainly dibutyl ether and butyl acetate. The lights stream is sent via line 5 to waste treatment and the tails stream is recycled via line 6 back to either or both of reactors 100 and 200. The design of distillation column 320 is consistent with conventional engineering practice and can use packing or trays. The base temperature of distillation column 320 is about 800° C. with a pressure of about 300 mmHg (0.4 bar absolute).

The tails fraction from splitter distillation column 310 is supplied via line 4 to distillation column 330. Column 330 separates the tails fraction into an overhead stream of butyl acrylate and a tails stream of heavies. The tails stream is recycled via line 8 to either or both of reactors 100 and 200 or is recycled to the distillation columns (not shown). The tails stream also contains inhibitors which, as described earlier, are desirably recycled. The column design is consistent with conventional engineering practice and can use packing or trays. The base temperature of the column is about 100° C. with a pressure of about 100 mmHg (0.2 bar absolute).

Employing the process of the present invention, a butyl acrylate product can be produced having the preferred composition as described in Table 8, above. Acrylates with such low levels of lights, especially dibutyl ether, exhibit significantly reduced odor as compared to commercially available acrylates and enable the production of unexpectedly high quality product from lower quality feedstock. This combination of improved quality and lower production cost has not been heretofore appreciated. Moreover, this invention enables the production of large quantities of butyl acrylate of a quality heretofore unavailable; i.e., commerical quantities of butyl acrylate in amounts of at least 10,000 lbs (avoir). Utilizing the process of the present invention, commercial scale quantities of butyl arylate product exhibit not only the preferred composition as reported in the second column of Table 8, above, but also, and more preferably, are of a composition which is at least 99.8wt % butyl acrylate and contains not more than about 200 ppm butyl ether, not more than about 100 ppm butyl acetate, not more than about 100 ppm butanol, and not more than about 200 ppm heavies (excluding propionates) and, most preferably, is at least 99.9wt % butyl acrylate and contains not more than about 150 ppm butyl ether, not more than about 50 ppm butyl acetate, not more than about 60 ppm butanol, and not more than about 200 ppm heavies (excluding propionates).

The following examples are intended to illustate one or more, but not all, embodiments within the scope of the present invention.

EXAMPLE 1

An embodiment of the invention employing two reactors was demonstrated using two 7 L reactors. Parenthetical reference to elements recited in FIG. 1 is included merely to further illustrate the operation of this embodiment of the invention; however, this example includes variations of the process not illustrated in FIG. 1 but which are fully envisioned by the invention as heretofore described. All quantities of materials and reaction products are approximate, resulting in a mass balance being about ±5%.

589 g/h of acrylic acid and 580 g/h of n-butanol were feed continuously to a first reactor (100), along with a 136 g/h stream (via 6) containing recycle butanol and inhibitor, and a 187 g/h recycle stream (via 9) from a second reactor (200) containing catalyst. Air was introduced into the first reactor at a rate of 9.4 sccm. The first reactor contained a 3.5 L liquid volume resident in the reactor for a period of 2 to 3 hours at a temperature of 129° C. and atmospheric pressure. A vapor stream rich in water was removed from the first reactor, sent to a first distillation column (120), condensed and decanted. The organic phase from the decanter was returned to the distillation column. The water phase from the decanter was sent to another distillation column (not illustrated in FIG. 1) at a rate of 144 g/h for further treatment, and the organic material contained in this stream was recovered and returned at a rate of 15 g/h to the first distillation column. A 1332 g/h liquid stream was also removed (via 1) from the first reactor and supplied to the second reactor.

The second reactor contained 3.5 L of liquid resident in the reactor for a period of 2 to 3 hours at a temperature of 133° C. and pressure of about 350 mm Hg absolute. Air was added to the second reactor at a rate of 94 sccm. Besides the liquid stream supplied from the first reactor, dodecylbenzene sulfonic acid (DBSA) diluted in butyl acrylate was added periodically at a rate that would equal 5 g/h on a continuous basis. A purge stream (via 10) was removed periodically from the second reactor at a rate that would equal 23 g/h on a continuous basis. A vapor stream was removed from the second reactor and was introduced into a distillation column (220). The distillation column was operated at a head temperature of 72° C. and pressure of 300 mm Hg. Air was added to the base of the distillation column at a rate of 94 sccm. Part of the bottoms distillation column's bottom stream (via 8) was recycled at a rate of 22 g/h to the top of the distillation column. The stream contained butyl acrylate with dilute inhibitor and heavy impurities. A water rich stream containing acrylic acid (via 15) was removed from the base of the distillation column and recycled to the second reactor at a rate of 1131 g/h. Vapor was removed from the top of distillation column, condensed and decanted. A portion of the organic phase, containing about 90 wt % butyl acrylate, was returned to the distillation column at a reflux to distillate ratio of 0.4 g/g, and a portion of the water phase was returned to the distillation column with a reflux to distillate ratio of 49.5 g/g. The remainder of the water phase, 19 g/h, was periodically returned to either the base of the distillation column ensure water was present to azeotrope the product out of the second reactor (200) and to keep the catalyst active, or sent to another distillation column (not illustrated in FIG. 1) for further treatment. The remainder of the organic stream, 1140 g/h, can be sent to a splitter distillation column (310) to produce, ultimately, essentially pure butyl acrylate.

The feedstock and stream compositions are reported in Table 9, below.

butyl acrylate stream containing inhibitor was fed to the top of the lights distillation column at rate of 6 g/h and air was introduced to the base column at a rate of 30 sccm. A vapor stream concentrated in light impurities was removed over head from the lights distillation column and a butanol rich steam was removed from the base of the lights distillation column. The vapor stream was condensed and decanted to yield an organic phase and water. A portion of the organic phase and water were returned to the column at a reflux to distillate ratio of 46.6 g/g. The remaining water from the decanter can be sent to another refining column (not shown

TABLE 9

| Component | AA Feed Wt % | BuOH Feed Wt % | DBSA Feed Wt % | Stream 1 Wt % | Stream 2 Wt % | Stream 6 Wt % | Stream 9 Wt % | Stream 10 Wt % | Stream 15 Wt % |
|---|---|---|---|---|---|---|---|---|---|
| Water | | | | 0.57 | 1.66 | 7.64 | 0.58 | 0.58 | 48.61 |
| Butanol (BuOH) | | 99.95 | | 12.49 | 8.46 | 69.41 | 0.40 | 0.40 | 0.51 |
| Acrylic Acid (AA) | 99.31 | | | 9.62 | 0.00 | 0.00 | 8.64 | 8.64 | 38.54 |
| Butyl Acrylate | | | 50.00 | 59.82 | 89.70 | 22.48 | 9.86 | 9.86 | 4.41 |
| BBP* + HVS** | | | | 8.17 | | 0.00 | 23.59 | 23.59 | 7.93 |
| Butyl Ether | | 0.01 | | 0.06 | 0.04 | 0.00 | 0.30 | 0.30 | |
| Butyl Acetate | | | | 0.09 | 0.12 | 0.09 | 0.00 | 0.00 | |
| DBSA | | | 50.00 | 0.71 | | | 4.53 | 4.53 | |
| Other | 0.69 | 0.04 | | 8.48 | 0.03 | 0.38 | 52.11 | 52.11 | |
| TOTAL | 100.00 | 100.00 | 100.00 | 100.00 | 100.00 | 100.00 | 100.00 | 100.00 | 100.00 |
| TOTAL, G/HR | 589 | 580 | 5 | 1332 | 1140 | 136 | 187 | 23 | 1131 |

*BBP = buytl-3-butoxypropionate
**HVS = butyl 3-acryloxy propionate and butyl propionic acid The 1140 g/h organic stream containing about 90 wt % butyl acrylate (via 2) was fed to the middle of splitter distillation column 310. A butyl acrylate stream containing inhibitor was fed at the top of the splitter distillation column at 53 g/h and air was introduced at the base of the splitter distillation column at a rate of 355 sccm. The splitter distillation column was operated at 150 mm Hg absolute head pressure and 71° C. head temperature. Butanol, butyl acrylate and light impurities were removed over head, and butyl acrylate with heavy impurities was removed from the base of splitter distillation column. The overhead from the splitter distillation column was condensed and decanted. A portion of the organic phase was returned to the column at a reflux to distillate ratio of 11.7 g/g and the remaining organic phase was sent (via 3) to a lights distillation column (320) at a rate of 113 g/h. The total water phase from the decanter can be sent to another refining column (not shown in FIG. 1) at a rate of 1 g/h. From the bottom of the splitter distillation column, a stream was removed (via 4) at an 1110 g/h rate and supplied to a bottoms distillation column 330.

The lights distillation column (320) was operated at 150 mm Hg head pressure and a head temperature of 55° C. A in FIG. 1) at a rate of 2 g/h. The remainder of the organic phase from the decanter is purged from the system at a rate of 4 g/h (via 5). The butanol rich stream from the bottom of the lights distillation column was removed (via 6) at 136 g/h can be returned to either or both of the first or second reactors.

The bottoms distillation column (330) was operated at 20 mm Hg head pressure and a head temperature of 53° C. Two butyl acrylate streams containing inhibitors were fed to the top of the column at rate of 5 g/h each, and air was introduced to the bottom of the column at a rate of 83 sccm. Vapor from the top of the bottoms distillation column was condensed and refluxed back to the column at a reflux to distillate ratio of 0.2 g/g. From the bottom of bottoms distillation column a stream was removed (via 8) at 59 g/h and can be recycled to either or both of the first or second reactors. From the top of bottoms distillation column (via 7) 99.9 wt % butyl acrylate was removed at 992 g/h.

The compositions of key streams taken from the reactor and distillation columns are reported in Table 10, below.

TABLE 10

| Component | Stream 2 Wt % | Stream 3 Wt % | Stream 4 Wt % | Stream 5 Wt % | Stream 6 Wt % | Stream 7 Wt % | Stream 8 Wt % |
|---|---|---|---|---|---|---|---|
| Water | 1.66 | 9.42 | 0.01 | 4.34 | 7.64 | 0.004 | 0.01 |
| Butanol | 8.46 | 69.51 | | 26.31 | 69.41 | | |
| Acrylic Acid | 0.00 | 0.00 | | | 0.00 | | |
| Butyl Acrylate | 89.70 | 19.54 | 99.76 | 23.56 | 22.48 | 99.982 | 98.10 |
| BBP + HVS | | | | | 0.00 | | 0.03 |
| Butyl Ether | 0.04 | 0.27 | | 7.63 | 0.00 | | |
| Butyl Acetate | 0.12 | 0.90 | | 36.08 | 0.09 | | |

TABLE 10-continued

| Component | Stream 2 Wt % | Stream 3 Wt % | Stream 4 Wt % | Stream 5 Wt % | Stream 6 Wt % | Stream 7 Wt % | Stream 8 Wt % |
|---|---|---|---|---|---|---|---|
| Other | 0.03 | 0.35 | 0.23 | 2.08 | 0.38 | 0.01 | 1.86 |
| TOTAL | 100.00 | 100.00 | 100.00 | 100.00 | 100.00 | 100.00 | 100.00 |
| TOTAL, G/HR | 1140 | 113 | 1110 | 4 | 136 | 992 | 59 |

EXAMPLE 2

576 g/h of acrylic acid and 599 g/h of n-butanol are feed continuously to a first reactor (100), along with a 137 g/h stream (Stream 6) containing recycle butanol and inhibitor, and a 156 g/h recycle stream (Stream 9) from a second reactor containing catalyst. The first reactor (100) contains 3.5 L liquid resident in the reactor for a period of 2 to 3 hours at a temperature of 129° C. and atmospheric pressure. A vapor stream rich in water is removed from the first reactor, is sent to a first distillation column, and is then condensed and decanted. The water phase is sent to another distillation column (not illustrated in FIG. 1) for further treatment, and the organic phase is returned to the first distillation column. A 1339 g/h liquid stream (Stream 1) is removed from the first reactor and is supplied to the second reactor.

The second reactor (200) contains 3.5 L liquid resident in the reactor for a period of 2 to 3 hours at a temperature of 133° C. and pressure of about 350 mm Hg absolute. Besides the liquid stream being fed from the first reactor, dodecylbenzene sulfonic acid (DBSA) diluted in butyl acrylate is added at a rate of 3 g/h. A recycle stream (Stream 10) is removed from the second reactor at a rate of 27 g/h. A vapor stream is removed from the second reactor and is introduced into a distillation column. The distillation column is operated at a head temperature of 72° C. and pressure of 300 mm Hg. A water rich stream containing acrylic acid (Stream 15) is removed from the base of the distillation column and is recycled to the second reactor at a rate of 1061 g/h. Vapor is removed from the top of distillation column, and is then condensed and decanted. A portion of the organic phase, containing about 90 wt % butyl acrylate, is returned to the distillation column. The remainder of the organic stream, 1151 g/h, is sent to a splitter distillation column to produce, ultimately, essentially pure butyl acrylate.

The 1151 g/h organic stream (Stream 2) is fed to the middle of the splitter distillation column. The splitter distillation column is operated at 150 mm Hg absolute head pressure and 71° C. head temperature. Butanol, butyl acrylate and light impurities are removed over head, and butyl acrylate with heavy impurities is removed from the base of splitter distillation column. The overhead from the splitter distillation column is condensed and decanted. A portion of the organic phase is returned to the column and the remaining organic phase (Stream 3) is sent to a lights distillation column at a rate of 143 g/h. The total water phase from the decanter is sent to another refining column at a rate of 3 g/h. From the bottom of the splitter distillation column, a stream (Stream 4) is removed at an 1005 g/h rate and is supplied to a bottoms distillation column 330.

The lights distillation column (320) is operated at 150 mm Hg head pressure and a head temperature of 55° C. A vapor stream concentrated in light impurities is removed over head from the lights distillation column and a butanol rich steam is removed from the base of the lights distillation column. The vapor stream is condensed and is decanted to yield an organic phase and water. A portion of the organic phase and water are returned to the column. The remaining water from the decanter is sent to another refining column at a rate of 2 g/h. The remainder of the organic phase from the decanter is purged from the system at a rate of 4 g/h (Stream 5). The butanol rich stream (Stream 6) from the bottom of the lights distillation column is removed at 137 g/h and is returned to either or both of the first or second reactors.

The bottoms distillation column is operated at 20 mm Hg head pressure and a head temperature of 53° C. Vapor from the top of the bottoms distillation column is condensed and is refluxed back to the column at a reflux to distillate ratio of 0.2 g/g. From the bottom of bottoms distillation column a stream (Stream 8) is removed at 7 g/h and is recycled to either or both of the first or second reactors. From the top of bottoms distillation column 99.9 wt % butyl acrylate is removed at 998 g/h.

The compositions of key feedstocks, and compositions of reaction and product streams taken from the reactors and distillation columns, are reported in Table 11, below.

TABLE 11

| Component | AA Feed Wt % | BuOH Feed Wt % | DBSA Feed Wt % | Stream 1 Wt % | Stream 2 Wt % | Stream 3 Wt % | Stream 4 Wt % | Stream 5 Wt % | Stream 6 Wt % | Stream 7 Wt % | Stream 8 Wt % | Stream 9 Wt % | Stream 10 Wt % | Stream 15 Wt % |
|---|---|---|---|---|---|---|---|---|---|---|---|---|---|---|
| Water | 0.04 | 0.10 | | 0.71 | 1.21 | 9.22 | 0.00 | 3.23 | 8.08 | 0.00 | 0.00 | 0.90 | 0.90 | 82.04 |
| Butanol (BuOH) | | 99.85 | | 12.29 | 8.19 | 64.65 | 0.00 | 35.52 | 66.35 | 0.00 | 0.00 | 0.40 | 0.40 | 0.29 |
| Acrylic Acid (AA) | 99.91 | | | 6.62 | 0.00 | 0.00 | 0.00 | | | 0.00 | 0.00 | 10.00 | 10.00 | 11.88 |
| Butyl Acrylate | | | | 69.02 | 90.46 | 24.99 | 99.89 | 20.31 | 25.37 | 99.99 | 84.30 | 6.00 | 6.00 | 1.16 |
| BBP + HVS | | | | 10.04 | 0.00 | 0.00 | 0.10 | | | 0.00 | 15.70 | 72.60 | 72.60 | 4.63 |
| Butyl Ether | | | 0.05 | 0.08 | 0.08 | 0.61 | 0.01 | 21.63 | 0.05 | 0.01 | 0.00 | 0.10 | 0.10 | 0.00 |

TABLE 11-continued

| Component | AA Feed Wt % | BuOH Feed Wt % | DBSA Feed Wt % | Stream 1 Wt % | Stream 2 Wt % | Stream 3 Wt % | Stream 4 Wt % | Stream 5 Wt % | Stream 6 Wt % | Stream 7 Wt % | Stream 8 Wt % | Stream 9 Wt % | Stream 10 Wt % | Stream 15 Wt % |
|---|---|---|---|---|---|---|---|---|---|---|---|---|---|---|
| Butyl Acetate | | | | 0.06 | 0.07 | 0.52 | 0.00 | 19.32 | 0.15 | 0.00 | 0.00 | | 0.00 | 0.00 |
| Acetic Acid | 0.05 | | | 0.00 | | | | | | | | | 0.00 | |
| DBSA | | | 100.00 | 1.17 | | | | | | | | 10.00 | 10.00 | |
| TOTAL | 100.00 | 100.00 | 100.00 | 100.00 | 100.00 | 100.00 | 100.00 | 100.00 | 100.00 | 100.00 | 100.00 | 100.00 | 100.00 | 100.00 |
| TOTAL, G/HR | 576 | 599 | 3 | 1339 | 1151 | 143 | 1005 | 4 | 137 | 999 | 7 | 156 | 27 | 1062 |

We claim:

1. A process for refining a butyl acrylate-containing stream comprising butyl acrylate, dibutyl ether, butyl acetate, heavies and butanol, the process comprising the steps of:
   a. introducing said stream into a splitter distillation column to provide an overhead fraction comprising dibutyl ether, butyl acetate, butyl acrylate and butanol and a bottoms fraction comprising butyl acrylate and heavies;
   b. withdrawing from the splitter distillation column the bottoms fraction; and
   c. separating heavies from said bottom fraction by introducing the bottoms fraction into a butyl acrylate distillation column to provide an overhead product containing butyl acrylate and a bottom product containing heavies.

2. The process of claim 1 further comprising the step of withdrawing from the butyl acrylate distillation column the overhead product.

3. The process of claim 2, further comprising the steps of:
   d. withdrawing from the splitter distillation column the overhead fraction; and
   e. introducing the overhead fraction into a butanol recovery distillation column to provide an overhead stream comprising dibutyl ether and butyl acetate and a bottoms stream comprising butanol; and
   f. withdrawing from the butanol recovery distillation column the bottoms stream.

4. The process of claim 1, wherein the stream introduced into the splitter column further comprises water.

5. The process of claim 4, wherein the overhead fraction from the splitter distillation column further comprises azeotropes of at least one of dibutyl ether and butyl acetate.

6. A process for refining an acrylate containing stream comprising ether, acetate, heavies and alcohol, the process comprising the steps of:
   a. introducing said stream into a splitter distillation column to provide an overhead fraction comprising ether, acetate, acrylate and alcohol and a bottoms fraction comprising acrylate and heavies;
   b. withdrawing from the splitter distillation column the bottoms fraction; and
   c. separating heavies from said bottom fractions by introducing the bottoms fraction into an acrylate distillation column to provide an overhead product containing acrylate and a bottom product containing heavies.

7. A process for the production of butyl acrylate, comprising the steps of:
   a. reacting in at least one reaction zone an acrylic acid-containing feedstock with a butanol-containing feedstock to produce a butyl acrylate-containing product stream comprising butyl acrylate, dibutyl ether, butyl acetate, heavies and butanol;
   b. introducing said product stream into a splitter distillation column to provide an overhead fraction comprising dibutyl ether, butyl acetate, butyl acrylate and butanol and a bottoms fraction comprising butyl acrylate and heavies;
   c. withdrawing from the splitter distillation column the bottoms fraction;
   d. separating heavies from said bottom fraction by introducing the bottoms fraction into a butyl acrylate distillation column to provide an overhead product containing butyl acrylate and a bottom product containing heavies.;
   e. withdrawing from the splitter distillation column the overhead fraction; and
   f. introducing the overhead fraction into a butanol recovery distillation column to provide an overhead stream comprising dibutyl ether and butyl acetate and a bottoms stream comprising butanol;
   g. withdrawing from the butanol recovery distillation column the bottoms stream; and
   h. supplying at least a portion of the bottom stream to said at least one reaction zone.

8. The process of claim 7, wherein water is supplied at least initially to said at least one reactor zone.

9. The process of claim 7, wherein the reaction of the feedstocks occurs in the presence of a homogeneous catalyst.

10. The process of claim 7, wherein there are at least two reaction zones, at least one of such reaction zones maintaining conditions under which at least a portion of the heavies are able to be cracked, and wherein at least a portion of the bottoms stream is supplied to said at least one reaction zone maintaining such conditions.

11. At least ten thousand pounds (avoir) of a butyl acrylate product comprising at least 99.8wt % butyl acrylate and containing not more than about 200 ppm butyl ether and not more than about 200 ppm butyl acetate.

12. The butyl acrylate product of claim 11 wherein the product further contains not more than about 200 ppm heavies (excluding propionates).

13. The butyl acrylate product of claim 11 wherein the product further contains not more than about 60 ppm butanol.

14. The butyl acrylate product of claim 11 comprising at least 99.9wt % butyl acrylate.

15. The butyl acrylate product of claim 12 comprising at least 99.9wt % butyl acrylate.

16. The butyl acrylate product of claim 11 containing not more than about 150 ppm butyl ether and not more than about 150 ppm butyl acetate.

17. The butyl acrylate product of claim 14 wherein the product contains not more than about 150 ppm butyl ether and not more than about 150 ppm butyl acetate.

* * * * *